US00PP32298P2

(12) United States Plant Patent
Olesen

(10) Patent No.: US PP32,298 P2
(45) Date of Patent: Oct. 13, 2020

(54) COMPACT FLORIBUNDA ROSE PLANT NAMED 'POULPAL080'

(50) Latin Name: ***Rosa* hybrid**
Varietal Denomination: Poulpal080

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/602,256

(22) Filed: Sep. 4, 2019

(51) Int. Cl.
*A01H 5/02* (2018.01)
*A01H 6/74* (2018.01)

(52) U.S. Cl.
USPC ..... Plt./141

(58) Field of Classification Search
USPC ..... Plt./141
CPC ..... A01H 5/02; A01H 6/74
See application file for complete search history.

(56) References Cited

PUBLICATIONS https://www.poulsenroser.dk/en/roses/ShowProduct/55461?productGroup=PAL 2020.*
PLUTO Plant Variety Database Mar. 6, 2020. p. 1.*

* cited by examiner

*Primary Examiner* — Annette H Para

(57) ABSTRACT

A new garden rose plant of the Compact Floribunda class which has abundant, apricot and pink blend flowers and attractive foliage. This new and distinct variety has shown to be uniform and stable in the resulting generations from asexual propagation.

3 Drawing Sheets

Botanical designation: *Rosa* hybrid.
Variety denomination: 'Poulpal080'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2010 and the resulting seeds were planted in a controlled environment in Fredensborg, Denmark. The new variety, named 'Poulpal080', originated as a single seedling from the stated cross.

The new variety may be distinguished from its male pollen parent and female seed parent primarily by the following characteristics. The male pollen parent plant has orange flowers while the new variety has apricot and pink blend flowers. The female seed parent plant has medium pink flowers while the new variety has apricot and pink blend flowers.

The objective of the hybridization of this rose variety was to create a new and distinct variety with unique qualities, such as:

1. Uniform and abundant apricot and pink blend flowers;
2. Vigorous, but compact growth when propagated on its own roots;
3. Exceptional disease resistance.

This combination of qualities is not present in previously available commercial cultivars of this type, known to the inventor, and distinguish 'Poulpal080' from all other varieties of which we are aware.

As part of the rose development program, Mogens N. Olesen germinated the seeds from the aforementioned hybridization during winter of 2010 and conducted evaluations on the resulting seedlings in a controlled environment in Fredensborg, Denmark. 'Poulpal080' was selected in the spring of 2011 by the inventor as a single plant from the progeny of the aforementioned hybridization.

Asexual reproduction of 'Poulpal080' by rooted cuttings was first done by Mogens N. Olesen in the nursery in Fredensborg, Denmark in July, 2011. This initial and other subsequent asexual propagations conducted in controlled environments have demonstrated that the characteristics of 'Poulpal080' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpal080'.

Specifically illustrated in FIG. 1 of the drawings are open flowers, petals detached showing reproductive flower parts.

Figure 1:
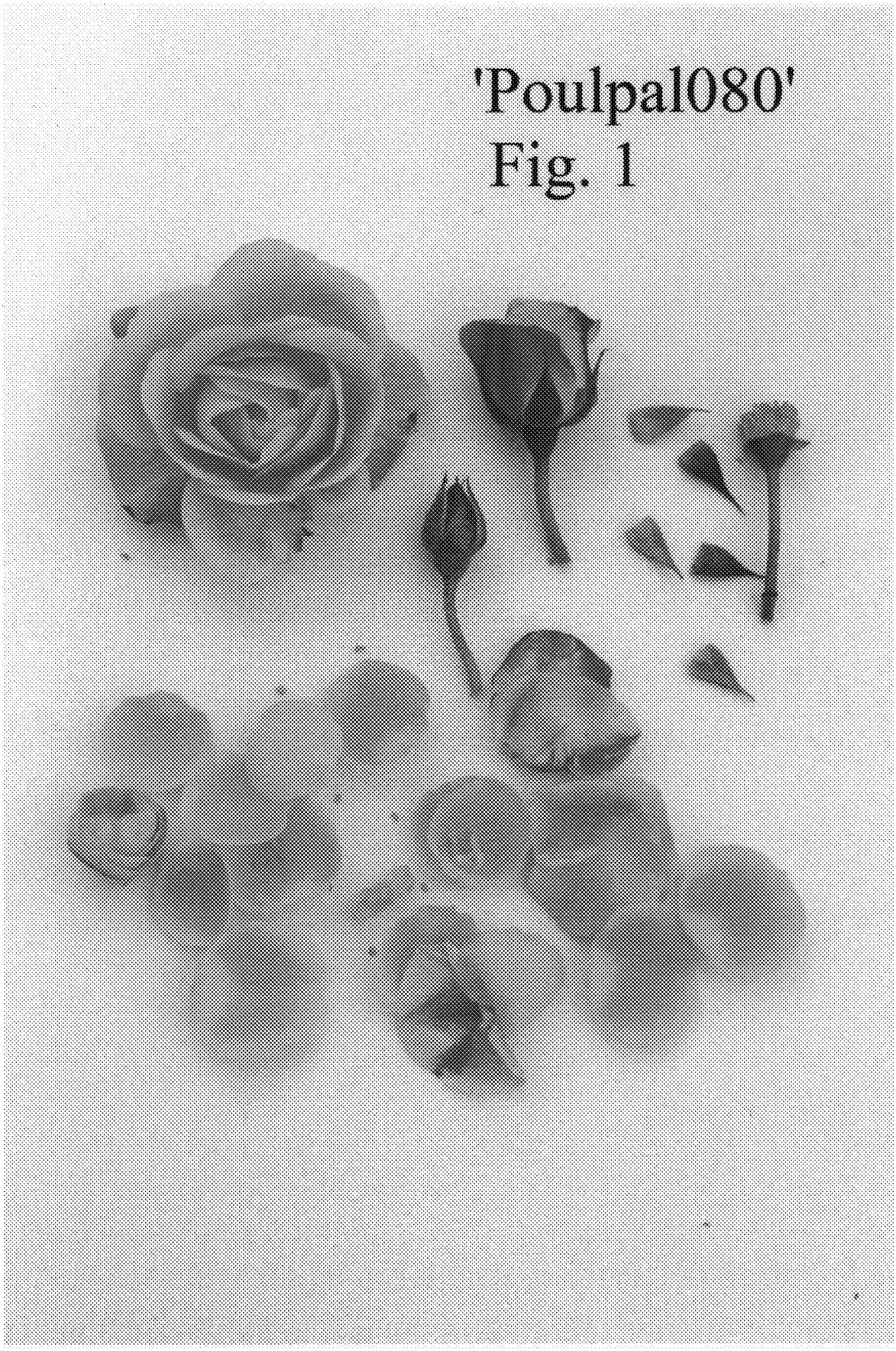
Figure 2:
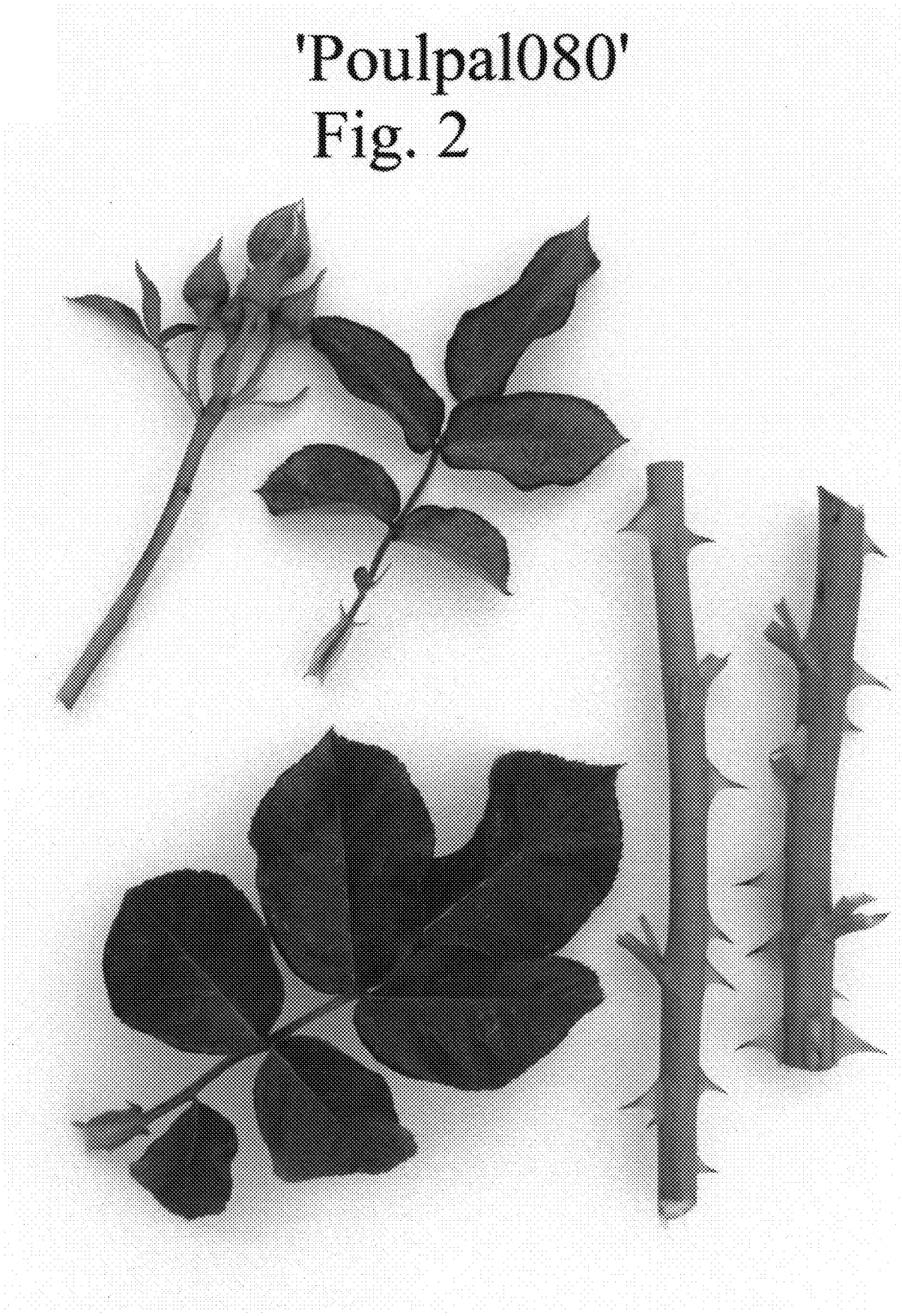

Specifically illustrated in FIG. 2 of the drawings are leaves and stems.

Figure 3:
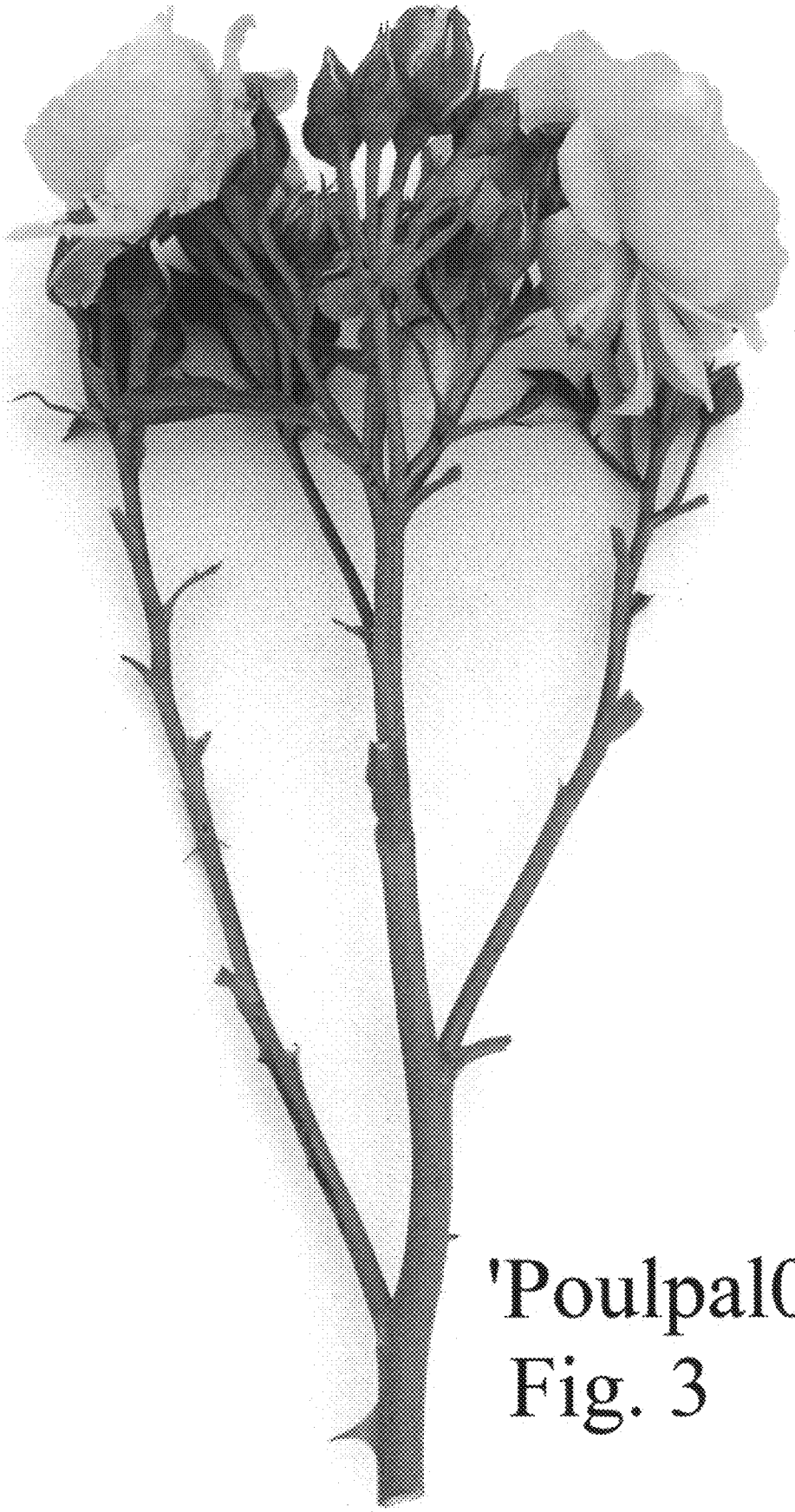

Specifically illustrated in FIG. 3 of the drawings is a cluster of flowers on a branch. Plants shown are 2 years of age.

DETAILED DESCRIPTION OF THE VARIETY

The following is a description of 'Poulpal080', as observed in its growth in a field nursery in Linn County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulcas024', U.S. Plant Pat. No. 16,961 are compared to 'Poulpal080' in Chart 1.

CHART 1

| | 'Poulpal080' | 'Poulcas024' |
|---|---|---|
| Petal Count | 42 petals | 300 petals |
| Flower Diameter | 65 mm | 40 mm |
| General Tonality of Flower Color | Yellow-Orange Group 16B | Red Group 49A to 49B |

FLOWER AND FLOWER BUD

Blooming habit: Continuous.

Flower bud:

*Size.*—Upon opening, 20 mm in length from base of receptacle to end of bud. Bud diameter is 13 mm.

*Bud form.*—Ovoid.

*Bud color.*—As sepals divide petals are Orange-Red Group N34A, Orange-Red Group N34C, and Yellow Group 8B.

*Sepal inner surface.*—Color: Yellow-Green Group 146D. Surface: Weak pubescence.

*Sepal outer surface.*—Color: Yellow-Green Group 144A with intonations of Greyed-Red Group 181A. Texture: Rough, with stipitate glands.

*Sepal shape.*—Apex: Cirrhose. Base: Flat at union with receptacle.

*Sepal margin.*—Margins have weak foliaceous appendages on three of the five sepals.

*Sepal size.*—21 mm long, 7 mm wide.

*Receptacle.*—Texture: Smooth. Size: 5 mm in height, 8 mm wide. Color: Yellow-Green Group 144A with intonations of Greyed Red Group 181B. Shape: Campanulate.

*Pedicel.*—Surface: Slightly rough with stipitate glands. Length: 25 mm. Diameter: 2 mm on average. Color: Yellow-Green Group 144A. Strength: Strong.

*Peduncle.*—Length: 2 to 17 cm. Diameter: About 4 mm. Color: Yellow-Green Group 144A and anthocyanin, Greyed-Red Group 181A. Texture: Slightly rough with stipitate glands.

Flower bud development: Flower buds are borne in clusters of 5 up to 7 flower buds per stem.

Flower bloom:

*Fragrance.*—Moderate, honey like.

*Duration.*—The blooms have a duration on the plant of approximately 10 days. Petals fall cleanly away from plant after flowers have fully matured.

*Size.*—Flower diameter is 65 mm when open. Flower depth is 30 mm.

*Flower shape.*—Hybrid tea like flower with double petalage.

*Shape of flower, side view.*—The upper portion is flat. The lower portion is concave.

Petalage: Under normal conditions, flowers have about 35 petals.

General tonality of flower: Open flowers are Yellow-Orange Group 16B.

Petal color:

*Upon opening, outer petals.*—Upper surface: Yellow-Orange Group 16D splashed with Orange Group 24C. Lower surface: Yellow Group 10B splashed with Red 45C and Red Group 48B.

*Upon opening, inner petals.*—Upper surface: Yellow Group 10B splashed with Orange Group 26C. Lower surface: Yellow Group 8B shaded lightly with Yellow-Orange Group 22C.

*Basal petal spots, upon opening.*—Upper surface: Yellow Group 7A. Lower surface: Yellow Group 8A.

*After opening, outer petals.*—Upper surface: Yellow Group 10C, splashed with Orange Group 24C. Lower surface: Yellow Group 10B. At the basal zone is Yellow Group 8A.

*After opening, inner petals.*—Upper surface: Yellow Group 10C, splashed with Orange Group 24C. Lower surface: Yellow Group 10B. At the basal zone is Yellow Group 8A.

*Basal petal spots, after opening.*—Upper surface: Yellow Group 7A. Lower surface: Yellow Group 8A.

Petals:

*Petal reflex.*—Weak.

*Margin.*—Entire and uniform. Moderate undulations.

*Shape.*—Broad and elliptic. Apex shape: Rounded. Base shape: Acute.

*Size.*—35 mm (l)×36 mm (w).

*Texture.*—Smooth.

*Thickness.*—Average.

Petaloids:

*Size.*—16 mm (l) by 15 mm (w).

*Quantity.*—7 to 9.

*Shape.*—Rounded, with a rounded base and rounded apices.

*Color.*—

*Margin undulations.*—Strong.

Reproductive flower parts:

*Pollen.*—None observed.

*Anthers.*—Size: 1.5 mm in length. Color: Yellow-Orange Group 14A. Quantity: 43 on average.

*Filaments.*—Color: Yellow Group 12A. Length: 5 mm.

*Pistils.*—Length: 7 mm. Quantity: 15 on average.

*Stigmas.*—Color: Green Yellow Group 1C.

*Styles.*—Color: Green Yellow Group 1C.

*Location of stigmas.*—Inferior in location relative to the length of the filaments and the height of the anthers.

*Hips.*—None Observed.

PLANT

Plant growth: Upright, bushy. Plants are 45 cm in height, and 45 cm wide.

Stems:

*Color of juvenile growth.*—Yellow-Green Group 144B.

*Color of mature growth.*—Yellow-Green Group 144A.

*Length.*—Canes are about 20 cm from the base of the plant to the flowering portion.

*Diameter.*—About 10 mm.

*Internodes.*—On mature canes about 35 mm between nodes.

*Surface texture.*—Young wood: Smooth. Older wood: Smooth.

Long prickles:

*Incidence.*—11 prickles per 10 cm of stem.

*Size.*—Average length of prickles on mature stems is 10 mm.

*Shape.*—Upper portion is linear. Lower portion is concave.

*Color.*—Juvenile prickles: Greyed-Yellow Group 160A with intonations of Greyed-Purple Group 185A. Mature prickles: Greyed-Yellow Group 160A.

Plant foliage:

*Compound leaf.*—140 mm (l)×95 (w).

*Quantity.*—2 leaves per 10 cm of stem on average.

*Leaf bearing angle to the stem.*—45 degrees.

*Color of juvenile foliage.*—Upper side: Yellow-Green Group 144A with Greyed-Purple Group 183A at margins. Lower side: Yellow-Green Group 146C.

*Color of mature foliage.*—Upper side: Yellow-Green Group 147A. Lower side: Yellow-Green Group 147B.

Plant leaves and leaflets:

*Stipules.*—Size: 22 mm long, 5 mm wide. Quantity: 2 per compound leaf. Shape: Linear, slightly broad based with outward extending apices. Margins: Finely serrated. Color: Yellow-Green Group 144A.

*Petiole.*—Length: 35 mm. Diameter: 2 mm. Upper surface color: Yellow-Green Group 144A. Lower surface color: Yellow-Green Group 144A.

*Rachis.*—Length: 50 mm. Upper surface color: Yellow-Green Group 144A with intonations of Greyed-Purple Group 184B. Lower surface color:

*Leaflet.*—Quantity: Normally 5 occasionally 7 leaflets. Margins: Serrated. Size: Terminal leaflets are about 60 mm long, 40 mm wide. Shape: Generally elliptical. Base: Rounded. Apex: Mucronate. Texture: Smooth. Thickness: Average. Arrangement: Odd pinnate. Venation: Reticulate. Glossiness: Very glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

We claim:

1. A new and distinct variety of rose plant of the Compact Floribunda rose class named 'Poulpal080', substantially as illustrated and described herein, due to its abundant apricot and pink blend flowers, disease resistance, and extended period of bloom.

* * * * *

'Poulpal080'

'Poulpal080'

'Poulpal080'